United States Patent
Wilhelm et al.

(10) Patent No.: US 9,506,893 B2
(45) Date of Patent: Nov. 29, 2016

(54) POTENTIOMETRIC PROBE FOR MEASURING A MEASURED VARIABLE OF A MEDIUM IN A CONTAINER

(75) Inventors: Thomas Wilhelm, Halle (DE); Thilo Trapp, Aliso Viejo, CA (US)

(73) Assignee: Endress+l lauser Conducta GmbH+Co. KG, Gerlingen (DE)

( * ) Notice: Subject to any disclaimer, the term of this patent is extended or adjusted under 35 U.S.C. 154(b) by 803 days.

(21) Appl. No.: 13/807,473

(22) PCT Filed: Jun. 20, 2011

(86) PCT No.: PCT/EP2011/060210
§ 371 (c)(1),
(2), (4) Date: Mar. 15, 2013

(87) PCT Pub. No.: WO2012/000818
PCT Pub. Date: Jan. 5, 2012

(65) Prior Publication Data
US 2014/0144776 A1    May 29, 2014

(30) Foreign Application Priority Data

Jul. 2, 2010  (DE) .......................... 10 2010 030 874

(51) Int. Cl.
*G01N 27/416* (2006.01)
*G01N 27/403* (2006.01)
*G01N 27/36* (2006.01)

(52) U.S. Cl.
CPC ...... *G01N 27/4161* (2013.01); *G01N 27/4035* (2013.01); *G01N 27/36* (2013.01)

(58) Field of Classification Search
None
See application file for complete search history.

(56) References Cited

U.S. PATENT DOCUMENTS 3,835,010 A * 9/1974 Levins .......................... 204/417
4,012,308 A * 3/1977 Jerrold-Jones ..... G01N 27/4035
                                                              204/408

(Continued)

FOREIGN PATENT DOCUMENTS

CH   680311 A5   7/1992
CN   1419651 A   5/2003

(Continued)

OTHER PUBLICATIONS

Crison pH, redox and I.S.E. electrodes, Apr. 2008.*

(Continued)

*Primary Examiner* — Luan Van
*Assistant Examiner* — Steven Rosenwald
(74) *Attorney, Agent, or Firm* — Christopher R. Powers; PatServe (57) ABSTRACT

A potentiometric probe, comprising: a housing, which has a first chamber, in which a reference half-cell is formed, which is in communication with a medium surrounding the housing via an electrolytic contact location arranged in a wall of the housing. The housing has a second chamber, in which a measuring half cell is formed, wherein the second chamber is closed on one end by a measuring membrane, such that a surface area of the measuring membrane facing away from the second chamber is in contact with the medium surrounding the housing, and wherein the measuring half cell has a lengthwise extension between the measuring membrane and a closure element bounding the measuring half cell on an end lying opposite the measuring membrane. A quotient of a separation of the measuring membrane from the closure element and an outer diameter of the housing amounts to less than 5, especially less than 2.

14 Claims, 4 Drawing Sheets

(56) References Cited

U.S. PATENT DOCUMENTS

| | | | |
|---|---|---|---|
| 5,147,524 A * | 9/1992 | Broadley | 205/787.5 |
| 5,393,391 A | 2/1995 | Dietze et al. | |
| 6,616,821 B2 * | 9/2003 | Broadley et al. | 204/435 |
| 7,491,303 B2 | 2/2009 | Sakata | |
| 8,043,490 B2 | 10/2011 | Auerswald | |
| 2003/0042150 A1 | 3/2003 | Ryu | |
| 2004/0244151 A1 * | 12/2004 | Sakata et al. | 23/306 |
| 2010/0176006 A1 * | 7/2010 | Bickford et al. | 205/792.5 |

FOREIGN PATENT DOCUMENTS

| | | | |
|---|---|---|---|
| CN | 1620607 A | 5/2005 | |
| CN | 101430326 A | 5/2009 | |
| CN | 101430327 A | 5/2009 | |
| CN | 101460834 A | 6/2009 | |
| DE | 100 22 210 A1 | 11/2001 | |
| DE | 102 14 713 A1 | 10/2003 | |
| DE | 20 2004 018 279 U1 | 3/2005 | |
| DE | 202004018279 * | 3/2005 | G01N 27/333 |
| EP | 0 449 166 A2 | 10/1991 | |
| GB | 2370646 A * | 3/2002 | G01N 27/30 |
| JP | 2001356110 A | 12/2001 | |
| WO | 2008/068274 A1 | 6/2008 | |
| WO | 2009/059645 A1 | 5/2009 | |
| WO | 2010/072509 A1 | 7/2010 | |

OTHER PUBLICATIONS

German Search Report in corresponding 10 2010 030 874.9, dated Jun. 14, 2011.

International Search Report in corresponding PCT/EP2011/060210, dated Oct. 24, 2011.

International Preliminary Report on Patentability in corresponding PCT/EP2011/060210, dated Jan. 17, 2013, English translation thereof.

* cited by examiner

POTENTIOMETRIC PROBE FOR MEASURING A MEASURED VARIABLE OF A MEDIUM IN A CONTAINER

TECHNICAL FIELD

The invention relates to a potentiometric probe for measuring a measured variable of a medium in a container, especially a flexible container, especially for applications in single use, measurements technology for biotech, biochemical, pharmaceutical or biological processes.

BACKGROUND DISCUSSION

Pharmaceutical, chemical, biological, biochemical or biotech processes are performed in increasing measure in single-use containers (also referred to as disposables, or disposable bioreactors). Such single-use containers can be, for example, flexible containers, e.g. bags, hoses or fermenters, respectively bioreactors. Bioreactors or fermenters possess, frequently, supply and drain lines, which can be embodied, for example, as hoses or flexible tubing. Applied in the supply and drain lines can also be rigid tubular pieces. After terminating a process, the single-use container can be disposed of. In this way, complex cleaning- and sterilization methods are avoided. Especially, through the use of single use containers, the risk of cross contaminations is avoided and therewith, bio- and process safety is increased. The single-use containers are, as a rule, produced from synthetic material, e.g. plastic.

The processes running in single-use containers are closed off from the environment. Since, frequently, sterile conditions are required, the single-use containers must be sterilized before introducing the process media. To this end, frequently, gamma radiation is used in biochemical, biological, biotechnological and pharmaceutical applications. Also, while the processes are running in a single-use fermenter or non-returnable reactor, the penetration of germs from the environment into the interior of the container must be prevented, in order not to degrade or corrupt the process.

In order to monitor or control the processes, it can be necessary to measure physical or chemical, measured variables of the media in the container. Monitored measured variables can include, for example, temperature, pH-value, cell density, optical transmission or concentration of a chemical substance, for example, a certain kind of ion or a certain element or a certain compound.

An opportunity for measuring at least some of these measured variables lies in the application of optical sensors. For example, there can be arranged in the flexible container active surfaces capable of being read out optically by sensor. These surfaces, which are referred to as 'optical sensor spots', can be scanned contactlessly from the outside through a window. The fluorescent dyes used for the sensor spots can, however, be sensitive to the gamma radiation frequently used in biotechnological and pharmaceutical applications for sterilization as well as also being sensitive to aggressive chemical conditions, such as can occur especially in the case of the purification of biotechnologically manufactured products.

European patent application EP 2 065 701 A2 describes probes, which can be arranged in a flexible, single-use container, and which can, via an inductive interface, exchange data with a measurement transmitter arranged outside of the container.

The measurement transmitter can also supply the probes with energy via the inductive interface. Data and energy can, in this way, be transmitted inductively through the container wall without requiring an opening for the probe or at least supply lines to the probe. In order to implement inductive transmission of data and energy between the probe and the measurement transmitter, electronic circuits are required, both on a primary side as well as also on a secondary side of the inductive interface. These circuits cannot withstand the gamma radiation used for sterilizing the flexible container and the probe.

International patent application WO 2009/071829 A2 and German Offenlegungsschrift DE 10 2006 005 533 A1 describe complex mechanical coupling systems, which enable sterile introduction of an externally sterilized probe into a single-use container.

Known from German Gebrauchsmuster DE 20 2007 000 152 U1 is an apparatus for securement of an optical probe to a container with flexible wall, in the case of which the probe lies with a rear surface portion on an inner side of the container wall and is led with a central piece through an opening of the container wall, wherein the central piece is affixed to the container wall by clamping.

SUMMARY OF THE INVENTION

An object of the invention is to provide a potentiometric probe, which is suitable for monitoring a physical or chemical, measured variable of a measured medium in a container, especially a flexible container, for example, a single use fermenter or a single use bioreactor, especially also in supply and drain lines to and from the container, and which is universally applicable in a large number of different single use articles used in the most varied of pharmaceutical, biotechnological, biological and biochemical methods.

In order to configure the use of a container serving as a single use fermenter or single use bioreactor especially simply, the potentiometric probe should be connected fixedly into the container before the sterilization, for example, by irradiation with gamma radiation, and remain there for the duration of its residence in inventory and its subsequent application. While the actual use of the single-use container may last only a few weeks, storage times in the order of magnitude of one or more years should be possible.

The object is achieved by a potentiometric probe for measuring a measured variable of a medium in a container, especially a single use bioreactor, or in a supply or drain line of the single use bioreactor, wherein the potentiometric probe comprises: a housing, which has a first chamber, in which a reference half-cell is formed, which is in communication with a medium surrounding the housing via an electrolytic contact location arranged in a wall of the housing, wherein the housing has a second chamber, in which a measuring half cell is formed, wherein the second chamber is closed on one end by a measuring membrane, such that a surface area of the measuring membrane facing away from the second chamber is in contact with the medium surrounding the housing, and wherein the measuring half cell has a lengthwise extension between the measuring membrane and a closure element bounding the measuring half cell on an end lying opposite the measuring membrane, wherein a quotient of a separation of the measuring membrane from the closure element and an outer diameter of the housing amounts to less than 5, especially less than 2.

If the measuring membrane is curved, then the separation of the measuring membrane from the closure element means the separation between a peak of the membrane, i.e. between that point of the measuring membrane, which is farthest removed from the closure element, and the oppositely lying, closure element, which can be formed, for example, by a wall of the housing lying opposite the measuring membrane.

The separation of the measuring membrane from the closure element corresponds to the length of the measuring half cell in the direction of its lengthwise extension. The quotient of the length of the measuring half cell and the outer diameter of the housing represents thus an aspect ratio of the length of the probe to its diameter. If the quotient of the separation of the measuring membrane from the closure element divided by the outer diameter of the housing amounts to 5, then said separation is thus five times longer than the outer diameter of the housing. In the case of a quotient of 2, the separation of the measuring membrane from the closure element is correspondingly twice as long as the outer diameter of the housing. When the aspect ratio is less than 5, preferably less than 2, or even still less, then the shape of the potentiometric probe is relatively squat in comparison to usual rod-shaped potentiometric probes used in industrial process measurements technology, such as, for example, pH-single-rod, measuring chains, also referred to as combination electrodes, which usually have an outer diameter of 12 mm and a length of 120 mm or more.

Such a "squat" probe can be applied in a large number of different single use products used in biochemical, biological, pharmaceutical and biotechnological processes, since it claims much less space compared with a rod-shaped potentiometric measuring probe, and so can be installed into the wall of many different containers of most varied geometry, e.g. in bags, hoses, tubular inserts and other, lines. A squat probe can also be used advantageously for monitoring a measured medium present in a flexible container. It can be secured by means of a connection provided in a wall of the flexible container or correspondingly in a supply or drain line of the container. The flexible container with the installed probe can be sterilized by irradiation with gamma rays. Then, the flexible container can be stored in a folded state, wherein the probe remains in the container wall during the storage. The squat construction of the probe significantly lessens the danger of damage compared with a conventional, rod-shaped probe, which, due to shear forces, which, in the case of moving the container, for example, in the case of folding it together for storage, act on the rod, can easily be damaged and break.

The squat probe can be fitted into various connectors, for example, by inserting it into a suitable molded part, which has connecting means complementary to a connector of the single use container. In this way, one can fit one and the same probe type easily for use in containers having different connector types. Also, the housing of the probe itself can be embodied as an exactly fitting complement for a connector of a container. Alternatively, it is also an option to weld the housing of the probe permanently into a single-use container or to bond it there with adhesive, without having to provide releasable connecting means for securement of the probe in the container wall.

The closure element bounding the measuring half cell on its end lying opposite the measuring membrane can be formed, for example, by a wall of the housing, especially a housing lid. It can, however, also be formed by a sealing element or a potting compound, which closes the end lying opposite the measuring membrane of the measuring half cell extending lengthwise within the second chamber. Especially, the second chamber can be sealed on its end lying opposite the measuring membrane by a potting compound. In this case, the potting compound forms the closure element.

The quotient of the separation of the measuring membrane from the closure element lying opposite the measuring membrane and the outer diameter of the housing amounts preferably to at least 0.1. In this way, a reference electrolyte volume sufficient for the short time of use of the probe is still assured, so that a sufficient stability of the potential of the reference half-cell is assured for the short time of use of the probe.

In a first embodiment, the first chamber can be embodied as an annular chamber surrounding the second chamber, wherein the annular chamber is enclosed by an outer tubular housing wall and an inner tubular housing wall arranged concentrically to the outer tubular housing wall, as well as by two housing walls, especially annular, housing walls, lying opposite one another and extending perpendicularly to the tubular housing walls. This embodiment is thus similar to the arrangement of a conventional single-rod measuring chain.

In this embodiment, the measuring membrane can be connected fixedly with an inner end of the inner tubular housing wall, especially by adhesion, mechanical splicing or welding. The measuring membrane can also be adhered, mechanically spliced or welded directly to the lower housing wall lying perpendicular to the inner wall of the inner tubular housing wall. The measuring membrane can be especially an ion-selective membrane, for example, a pH-selective, glass membrane or a polymer- or solid membrane selective for a certain kind of ion. The measuring membrane can also be adhered directly on the inner wall of the inner tubular housing wall.

In case the measuring membrane is a pH-selective glass membrane, it can be welded to a glass tube, wherein the glass tube and the inner tubular housing wall are concentrically arranged, and wherein the glass tube is pressed into the inner tubular housing wall or adhered thereto, so that the glass membrane secured to the tube closes the second chamber on one end. The glass tube can be closed on the rear end by melting or by a sealing element. In these embodiments, the closure element bounding the measuring half cell on the end lying opposite the measuring membrane is formed by the melted location or the sealing element.

The glass tube can alternatively or supplementally be welded or adhered to a wall of the housing lying opposite the measuring membrane.

In an additional embodiment, the closure element bounding the measuring half cell on the end lying opposite the measuring membrane can be formed by a housing lid terminating the housing on its end facing away from the measuring membrane. The closure element can also be formed by a potting compound sealing the second chamber.

In an additional embodiment, the reference half-cell includes a reference electrolyte accommodated in the first chamber and a reference electrode immersed therein, which is connected with a first contact location arranged outside of the first chamber. The measuring half cell includes an internal electrolyte accommodated in the second chamber and, immersed therein, a potential sensing electrode, which is connected with a second contact location arranged outside of the second chamber. The contact locations are embodied, for example, each as a conductive coating on an outside of a housing wall, especially a housing lid. It is, however, also an option to provide, arranged on the outside of the housing wall, electrical plugs, which are connected, respectively, with the reference electrode and the potential sensing electrode.

Optionally in the second chamber, a temperature sensor can be provided, which is formed by a temperature dependent resistor. The connections of the temperature sensor are then likewise led through the housing wall to a contact location arranged outside of the housing. This contact location can be embodied in equal manner to the contact locations of the reference- and potential sensing electrodes.

The housing wall, on whose outside the contact locations are arranged, can be embodied as a circuit card, which includes vias, by way of which the potential sensing electrode and the reference electrode are connected with the outwardly lying, contact locations.

In the case, in which the closure element bounding the measuring half cell on its end lying opposite the measuring membrane is formed by a housing lid terminating the housing and/or the first and the second chambers on its, or their, end facing away from the measuring membrane, the housing lid can be embodied as a circuit card, which includes vias, by way of which the potential sensing electrode and the reference electrode are connected with the outwardly lying contact locations formed as printed, conductive traces or contact surfaces on the circuit card. In this case, the contacting of the reference electrode and the potential sensing electrode as well as, in given cases, a probe temperature sensor arranged in the second chamber can occur by a plug with spring contacts. Alternatively, a plug can be integrated permanently on the circuit card.

In an additional embodiment, there can be arranged on the circuit card in the form of electrical components, especially electrical resistors, a circuit, in which a characteristic, electrical parameter serving for sensor identification, especially a resistance value, is measurable. The electrical circuit is composed preferably of electrical components, which withstand sterilizing with gamma radiation. These include simple components, such as resistors and capacitors. In the circuit, a measurement transmitter connected with the probe can ascertain, for example, a characteristic value, for example, a certain resistance value, based on which the measurement transmitter can detect which type of probe is present.

In an additional embodiment, the inner electrolyte and the reference electrolyte can be embodied as electrolyte gels. Preferably, the gels are firm gels. In this embodiment, the probe can be used in any orientation, even upside down.

The probe includes a contact region comprising the measuring membrane and the electrolytic contact location. During the performing of measurements, the contact region is brought in contact with the measured medium, wherein the electrolytic contact location includes at least one pin of a porous material embedded within the contact region in the housing wall bounding the first chamber.

The electrolytic contact location can be formed by a plurality of pins of porous material embedded in the housing wall annularly around the measuring membrane. In this way, flow impingement effects, which occur, above all, in the case of low conductivities, are minimized. Examples of the porous material include synthetic material, e.g. PTFE or polypropylene, glass or ceramic, e.g. zirconium dioxide ceramic or aluminum oxide ceramic.

In an additional embodiment, the porous material has an average pore diameter of less than 200 nm. The small pore size avoids that microorganisms from the process penetrate through the diaphragm and into the first chamber and there cause a chemical change of the reference electrolyte.

The measuring membrane can be protected by one or more protective webs or a protective cage. In this way, the sensitive measuring membrane, for example, a pH-selective glass membrane, is protected against mechanical damage. The protective webs or the protective cage can be secured to the housing of the probe. It is also an option that the protective webs or the protective cage are provided secured on a connector for connecting the probe in the wall of a container in such a manner that they surround the measuring membrane after the intended connecting of the probe.

The housing of the probe can have connecting means, especially a screw thread, for connecting the probe with complementary connecting means, especially a complementary screw thread on the container for accommodating a measured medium. The connecting means can be formed directly on the housing of the probe; for example, the housing can have a cylindrical section, into which a screw thread is cut. Alternatively, the housing can also be inserted into a fitted jacket, which has the corresponding connecting means. Thus, different fitted jackets can be held in inventory, into which the housing of the probe is insertable, in order to fit the probe for application in the most varied of single-use containers of different geometries, especially single use fermenters, bags, hoses, tubular inserts, supply and drain lines for single use bioreactors, having differently embodied connecting means.

A container, especially a flexible, single-use container, for accommodating a measured medium, comprising at least one probe arranged in a container wall of the container and fashioned according to one of the above described embodiments, includes, in the container wall or in a supply line or in a drain of the container, a probe connection, which includes an opening and connecting means, which are embodied to be brought into engagement with complementary connecting means of the probe, so that the probe is held shape-interlockingly in such a manner in the opening that a contact region of the probe including the measuring membrane, the electrolytic contact location and a part of the outer surface of a housing wall bounding the first chamber on the side of the electrolytic contact location is in contact with the interior of the flexible container, while a connection region of the probe lying opposite the contact region is arranged outside of the flexible container.

In such case, the contact region is preferably sealed relative to the environment of the flexible container, for example, by means of a sealing ring, which, in the connected state of the connecting means of the probe and the complementary connecting means of the flexible container, is compressed in a seal seat, for example, a seal seat arranged on the connector of the container or on the probe.

BRIEF DESCRIPTION OF THE DRAWINGS

The invention will now be explained in greater detail based on the examples of embodiments illustrated in the drawing, the figures of which show as follows.

DETAILED DISCUSSION IN CONJUNCTION WITH THE DRAWINGS

Figure 1:
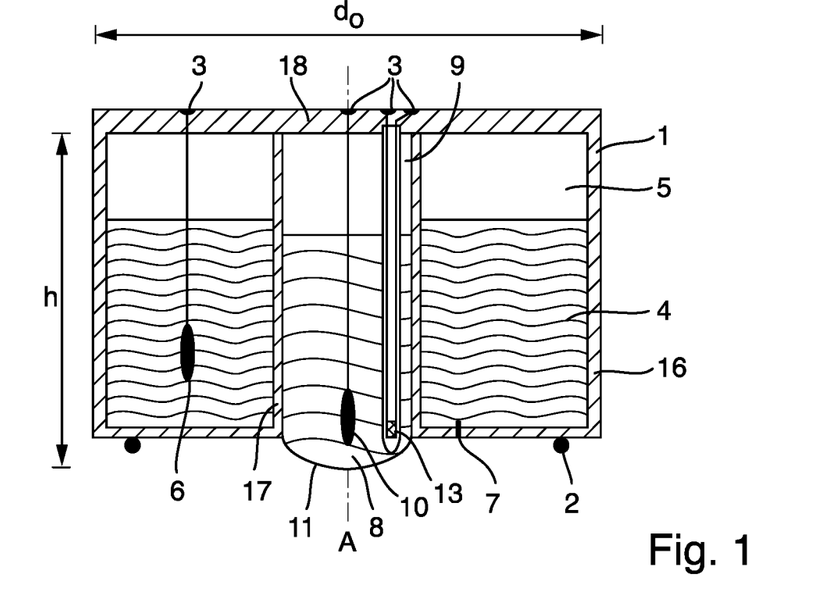
FIG. 1 is a schematic representation of a first example of a potentiometric probe.

FIG. 1 shows a potentiometric probe with a housing 1 of an insulating material. Housing 1 includes, embodied as an annular chamber, a first chamber 5, in which a reference half-cell is formed, and, surrounded by the annular chamber, an essentially cylindrical, second chamber 9, in which a measuring half cell is accommodated. The insulating material comprises especially a synthetic material, for example, polyetheretherketone (PEEK). The application of synthetic material for the housing makes the probe, on the one hand, almost unbreakable. On the other hand, such a housing of synthetic material can be produced price favorably with established injection molding methods, which is especially advantageous for the application of the probe as a single use part. The use especially of PEEK enables, besides sterilization by means of gamma radiation, also hot steam sterilization.

The first chamber 5 is surrounded by an outer tubular housing wall 16 and an inner tubular housing wall 17 arranged concentrically thereto, as well as by two annular housing walls, which lie opposite one another. The annular housing walls extend perpendicularly to the shared cylindrical symmetry axis A of the tubular housing walls 16, 17 and connect these with one another. The second chamber 9 is formed by the inner tubular housing wall 17 closed on its one end by the measuring membrane 11 and on its other end by a housing wall 18 lying opposite the measuring membrane 11. Accommodated in the first chamber 5 is a reference electrolyte 4, into which a reference electrode 6 extends. The reference electrolyte 4 can be, for example, a firm electrolyte gel. Preferably non toxic gels are used, e.g. gels, which contain no toxic monomers and which release no toxic monomers in the case of deterioration. A suitable electrolyte gel is given, for example, in international patent application WO 03/076917 A1. Reference electrode 6 is, for example, an Ag/AgCl, reference electrode in the form of a chlorided silver wire. The remaining space of the first chamber 5 not filled by the reference electrolytes 4, also referred to as compensation space, can contain air or even a polymer compensator, e.g. of silicone foam.

Arranged in the annular housing wall bounding the measuring membrane-side of the first chamber 5 and serving as electrolytic contact location, or liquid junction, is a diaphragm 7, via which the interior of the chamber 5, especially the therein accommodated reference electrolyte 4, is in communication with the environment of the housing 1. In measurement operation of the probe, diaphragm 7 provides an electrical, ionically conductive connection between the reference electrolyte 4 and the measured medium wetting the diaphragm 7. The electrolytic contact location can alternatively also be embodied as one or more bores in the housing wall or as an annular gap surrounding the measuring membrane 11. The diaphragm 7 can be embodied as a disk- or pencil-shaped insert of a porous material. In the example shown here, diaphragm 7 is embodied as a pin of a microporous ceramic, for example, a micropored, zirconium dioxide ceramic. In the present example, the measuring membrane 11 is a pH-selective, glass membrane. Preferably, the glass membrane is made of a low-ohm glass, which enables rapid response, even in the case of small glass membrane surfaces, and measurements using practically any measurement transmitter, so that the probe shown in FIG. 1 is universally applicable. The glass membrane 11 can be welded onto a glass tube, which is pressed into the inner tubular housing wall 17 surrounding the second chamber 9 or adhered with adhesive to the inner side of the housing wall 17. The glass tube can be closed on its end lying opposite the membrane; for example, it can be closed by melting or with adhesive, or it can be closed there by a sealing element.

If the potentiometric probe is embodied as an ion-selective electrode, the measuring membrane 11 can be a polymer membrane with or without softeners, conductive salts and/or ionophores. Such polymer membranes can be bonded with adhesive or welded directly to the inner cylindrical housing wall 17 from below or on its inside. Another option is a pressing in by means of a solid ring carrier against the inside of the inner tubular housing wall 17.

The second chamber 9 contains an internal electrolyte 8, into which a potential sensing electrode 10 extends. The inner electrolyte 8 can likewise be embodied, as the reference electrolyte 4, in the form of a firm electrolyte gel. Also, here, a non toxic, respectively a non toxic monomer containing or releasing, gel is preferred. The electrolyte lacking, compensation space of the second chamber 9 can contain air or a polymer compensator, e.g. silicone foam.

Arranged in the second chamber 9 in the example shown in FIG. 1 is, supplementally, a temperature sensor 13, which comprises a temperature dependent resistor arranged in a capillary tube of glass or synthetic material and so electrically insulated from the internal electrolyte 8. Temperature sensor 13 is only optionally present.

Housing 1 is composed in the example of an embodiment shown in FIG. 1 of an annular, injection molded part, which includes the outer tubular wall 16 and the inner tubular wall 17, as well as the diaphragm-side annular wall connecting the two tubular walls 16, 17 and a housing lid 18 bearing on the annular injection molded part and closing the first and second chambers 5, 9. The housing lid 18 forms here a wall lying opposite the measuring membrane 11 and serving as a closure element bounding the measuring half cell on its end lying opposite the measuring membrane 11.

The potential sensing electrode 10, the reference electrode 6 and the lines to the temperature sensor 13 are electrically conductively connected with contact locations 3 arranged outside of the first and second chambers of the housing 1. Contact locations 3 are arranged on the outside of the housing lid 18 in the example shown here. They can be, for example, electrically conductive coatings arranged on the outside of the housing lid 18. Contact locations 3 can be electrically conductively connected with a measurement transmitter, in order to perform measurements.

Housing lid 18 can, as in the example of FIG. 1, be made of the same material as the annular, injection molded part. Alternatively, the housing lid can also be embodied of an established circuit card, circuit board material, for example, phenolic resin+paper (FR1, FR2), epoxide resin paper (FR3), epoxide resin glass fiber weave (FR4, FR5), polyimide and/or polyester, or from electrically non conducting ceramic, a LTCC ceramic (Low Temperature Cofired Ceramic) or an Al2O3 ceramic, and have vias for electrically conductive connection of the potential sensing element 10, the reference electrode 6 and the connections of the temperature sensor 13. The vias can especially be connected electrically conductively with conductive traces or contact surfaces applied on the rear surface facing away from the housing interior. In this case, the contacting of the reference electrode 6, the potential sensing element 10 and the temperature sensor 13 occurs via a reusable plug with spring contacts (not shown).

The separation h between the closure element, formed here by the housing lid 18 bounding the measuring half cell on the end lying opposite the measuring membrane 11, and the point of the measuring membrane 11 most remote from the closure element, i.e. the peak of the measuring membrane 11, corresponds to the length of the chamber 9, i.e. the measuring half cell. The quotient of the separation h divided by the outer diameter $d_o$ of the outer tubular housing wall 16 extending perpendicular to the separation h, also referred to as the aspect ratio of the probe, amounts, in the example shown here, to, for instance, $h/d_o=0.6$. The outer diameter $d_o$ extends perpendicularly to the lengthwise extension of the measuring half cell and perpendicular to the cylindrical symmetry axis A of the outer tubular housing wall 16, respectively the inner tubular housing wall 17. In the example of FIG. 1, the outer diameter $d_o$ of the housing is formed by the outer diameter of the tubular housing wall 16.

With an aspect ratio of $h/d_o=0.6$, as in the example shown here, or, in general, with an aspect ratio of less than 2, the probe is, on the one hand, relatively squat in construction, while, on the other hand, the electrolyte volume in the reference- and measuring half cells is sufficient, at least for the short period of use of the potentiometric probe, in order to assure over the entire period of use a stable and reliable measurement signal.

Measuring membrane 11 is, in the present example, a glass membrane slightly curving convexly from the second chamber 9 of the housing 1. A glass membrane can also be more strongly convexly curved, however, it should preferably be, at a maximum, hemispherical, since the susceptibility to disturbances from gas bubbles in the measured medium is smaller than in the case of an almost spherical glass membrane. If the measuring membrane is an ion-selective solid body- or polymer membrane, it can be an essentially curvature free, flat membrane.

In the case of a flat membrane, the separation h between the measuring membrane and the closure element bounding the measuring half cell on the end lying opposite the measuring membrane is, to the extent that the closure element is formed by a planar wall as shown in FIG. 1, essentially identical for all points of the measuring membrane.

Figure 2:
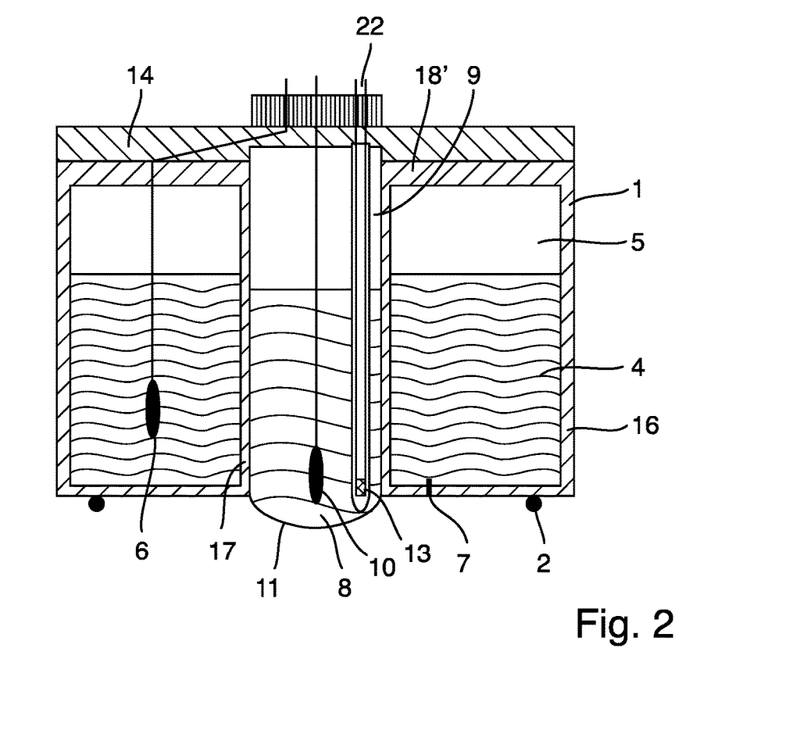
FIG. 2 is a schematic representation of a second example of a potentiometric probe, in the case of which the contacting of the half cells and of the temperature sensor occurs by means of a plug.

FIG. 2 shows a second example of an embodiment of a potentiometric probe, which is constructed essentially the same as the potentiometric probe shown in FIG. 1. Equal reference characters refer here to equal elements, or elements of the same type. In contrast to the probe shown in FIG. 1, the first chamber 5 is, on the connection side, closed by an annular housing lid 18', while the second chamber 9 is closed on the connection side by a potting compound 14. The closure element bounding the measuring half cell on the end lying opposite the measuring membrane 11 is thus formed in this example by the potting compound 14. The potting compound 14 surrounds and protects electrical lines, which lead from the potential sensing electrode 10, the reference electrode 6 and the temperature sensor 13 to a plug, which, in given cases, is at least partially potted with potting compound also. The plug has pins 22, which serve as contact locations arranged outside of the housing 1 for the potential sensing electrode 10, the reference electrode 6 and leads of the temperature sensor 13. The pins 22 can then be connected electrically conductively with a measurement transmitter for performing measurements.

Figure 3:
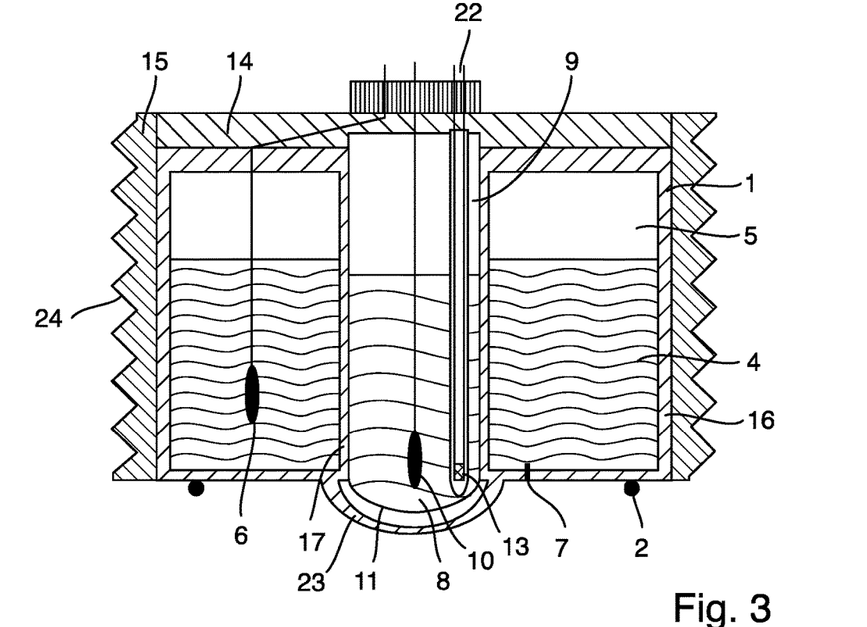
FIG. 3 is a schematic representation of a third example of a potentiometric probe, which is inserted into a fitted jacket having connecting means for affixing the probe in a wall of a container.

FIG. 3 shows a further example of an embodiment of a potentiometric probe, which is embodied essentially the same as the probe shown in FIG. 2. In contrast to the probe illustrated in FIG. 2, the housing 1 of the potentiometric probe shown in FIG. 3 includes, supplementally, a protective cage 23, which is secured to the annular housing wall bounding the first chamber 5 diaphragm-side, or is embodied as one-piece with such wall, and surrounds the measuring membrane to protect against mechanical damage.

In this case, also, the probe is integrated into a tubular, plastic, fitted jacket 15, which has a screw thread 24 on its cylindrical, outer wall. The plastic, fitted jacket 15 can be screwed into a connector provided on a flexible container, a connector which has a screw thread complementary to the screw thread 24. Such a connector can be provided, for example, on a flexible, single use fermenter or on a single use reactor or on a supply line or drain line of the single use fermenter or single use reactor, on a hose- or pipeline, on a tube insert or on some other single use container, which is intended for use in biotechnological processes.

The protective cage 23 can, in an alternative embodiment, also be secured to the plastic, fitted jacket 15.

The potentiometric probe has a contact region comprising the measuring membrane 11, the diaphragm 7 and a part of the diaphragm-side housing wall. The contact region is brought into contact with a measured medium for performing measurements of its pH-value. A container connector suitable for accommodating the probe integrated in the plastic, fitted jacket 15 includes a seal seat arranged, in the case of connected probe, on the diaphragm-side parallel to the annular housing wall bounding the first chamber 5. An O-ring-seal 2 is accommodated in the seal seat and seals the contact region from the environment of the container. In this way, hygienic conditions are assured within the container in the case of connected probe. Examples of materials for the O-ring-seal 2 include USP class IV-qualified materials.

Figure 4:
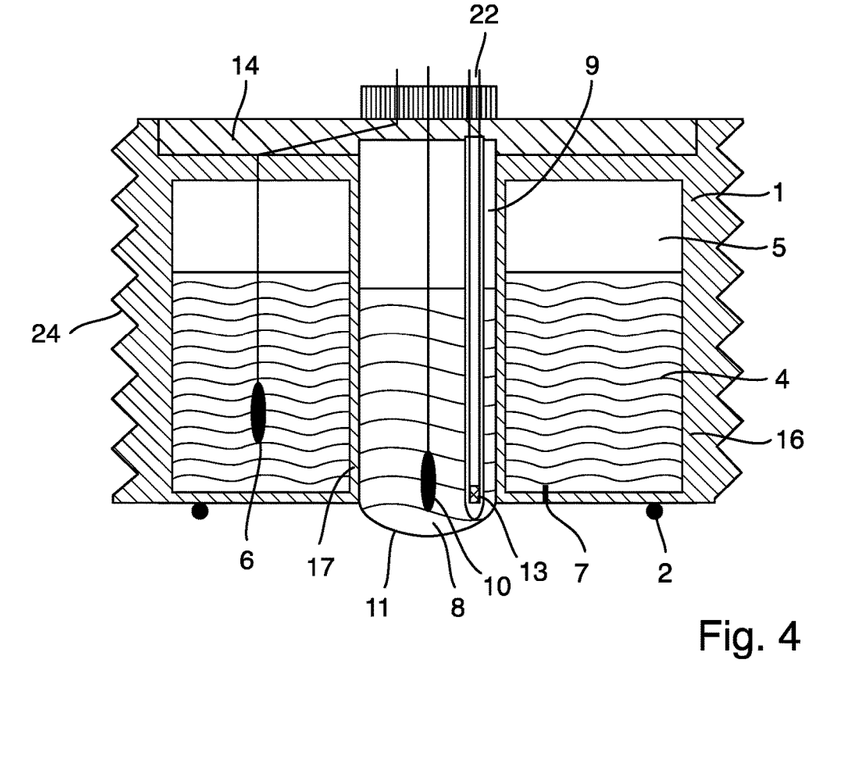
FIG. 4 is a schematic representation of a fourth example of a potentiometric probe, in the case of which the housing of the probe has connecting means for affixing the probe in a wall of a container.

Instead of integrating the probe in a separate, plastic, fitted jacket 15, which has corresponding securement means for connecting the probe to a connector arranged in a container wall, another option is to embody the probe in such a manner that the securement means are placed directly on the housing of the probe. For example, the housing outer wall of the probe can have a cylindrical section with a screw thread. This is shown in FIG. 4. In such case, the outer tubular housing wall 16 of the first chamber 5 has a screw thread 24.

The invention claimed is:

1. A potentiometric probe for measuring a measured variable of a medium in a container comprising:
   a housing, which has a first chamber in which a reference half-cell is formed, which is in communication with a medium surrounding said housing via an outwardly lying electrolytic contact location arranged in a wall of said housing, wherein;
   said housing has a second chamber, in which a measuring half-cell is formed, said second chamber is closed on one end by a measuring membrane, such that a surface area of said measuring membrane facing away from said second chamber is in contact with the medium surrounding said housing, wherein the housing further includes a closure element that at least partially defines the reference half-cell and the measuring half-cell;
   said first chamber is an annular chamber surrounding said second chamber,
   said measuring half-cell has a lengthwise extension between said measuring membrane and the closure element bounding said measuring half-cell on an end lying opposite said measuring membrane;
   a quotient of a separation distance of said measuring membrane from said closure element and an outer diameter of said housing is at least 0.1 to less than 2,
   said reference half-cell includes a reference electrolyte accommodated in said first chamber and a reference electrode immersed therein, which is connected with a first contact location arranged outside of the first chamber, said measuring half-cell includes an internal electrolyte accommodated in said second chamber and immersed therein, a potential sensing electrode, which is connected with a second contact location arranged outside of said second chamber; and said first and second contact locations are embodied, in each case, as conductive coatings on an outside of the closure element, wherein the closure element on whose outside said contact locations are arranged as conductive coatings, is embodied as a circuit card, which includes vias, by way of which said potential sensing electrode and said reference electrode are connected with said first and second contact locations, and said first and second contact locations are formed as printed, conductive traces or contact surfaces on the circuit card.

2. The potentiometric probe as claimed in claim 1, wherein:

said first chamber is embodied as an annular chamber surrounding said second chamber; and said annular chamber is enclosed by an outer tubular housing wall and an inner tubular housing wall arranged concentrically to said outer tubular housing wall, as well as by two housing walls, lying opposite one another and extending perpendicularly to the tubular housing walls.

3. The potentiometric probe as claimed in claim 2, wherein:

said measuring membrane is connected fixedly with an inner end of said inner tubular housing wall.

4. The potentiometric probe as claimed in claim 2, wherein:

said measuring membrane is a pH-selective glass membrane, which is welded to a glass tube;

said glass tube and said inner tubular housing wall are concentrically arranged;

said glass tube is pressed into said inner tubular housing wall or adhered thereto; and said glass tube can be closed, by melting or by a sealing element.

5. The potentiometric probe as claimed in claim 1, wherein:

said closure element lying opposite said measuring membrane is formed by a housing lid terminating said first and said second chamber on an end facing away from said measuring membrane, or said closure element lying opposite said measuring membrane is formed by a potting compound, an elastic sealing element or a melting of the glass tube.

6. The potentiometric probe as claimed in claim 1, wherein:

said inner electrolyte and said reference electrolyte are embodied as electrolyte gels.

7. The potentiometric probe as claimed in claim 1, wherein:

arranged on said circuit card in the form of electrical components is a circuit, in which a characteristic electrical parameter serving for sensor identification is measurable.

8. The potentiometric probe as claimed in claim 1, wherein:

an outer wall of the probe is provided with a plug connection, which includes contacts, via which said potential sensing electrode and said reference electrode are connected with outwardly lying, contact locations.

9. The potentiometric probe as claimed in claim 1, wherein:

the probe includes a contact region comprising said measuring membrane and said electrolytic contact location; and said electrolytic contact location includes at least one pin of a porous material, within the contact region in the housing wall bounding said first chamber.

10. The potentiometric probe as claimed in claim 9, wherein:

said electrolytic contact location is formed by a plurality of pins of porous material, embedded in said housing wall annularly around said measuring membrane or by a ring of porous material, embedded in said housing wall around said measuring membrane.

11. The potentiometric probe as claimed in claim 9, wherein:

the porous material has an average pore diameter of less than 200 nm.

12. The potentiometric probe as claimed in claim 1, wherein:

said measuring membrane is protected by one or more protective webs or by a protective cage.

13. The potentiometric probe as claimed in claim 1, wherein:

said housing has connecting means, for connecting the probe with connecting means of a probe connector arranged on the container, and complementary to the connecting means of the housing.

14. The potentiometric probe as claimed in claim 7, wherein the characteristic electrical parameter serving for sensor identification is a resistance value.

* * * * *

UNITED STATES PATENT AND TRADEMARK OFFICE
CERTIFICATE OF CORRECTION

PATENT NO. : 9,506,893 B2
APPLICATION NO. : 13/807473
DATED : November 29, 2016
INVENTOR(S) : Thomas Wilhelm et al.

Page 1 of 1

It is certified that error appears in the above-identified patent and that said Letters Patent is hereby corrected as shown below:

On the Title Page (73) Assignee should read: Endress+Hauser Conducta GmbH+Co. KG, Gerlingen (DE)

Signed and Sealed this
Twenty-eighth Day of March, 2017

Michelle K. Lee
*Director of the United States Patent and Trademark Office*